United States Patent [19]

Schoonen et al.

[11] Patent Number: 5,615,671
[45] Date of Patent: Apr. 1, 1997

[54] PROCESSES AND DEVICES FOR CONTINUOUSLY MONITORING LEVELS OF ANALYTE

[75] Inventors: Adelbert J. M. Schoonen, Groningen; Fransiscus J. Schmidt, Drachten; Klaas-Jan C. Wientjes, Groningen, all of Netherlands

[73] Assignees: Siemens-Elema AB, Solna, Sweden; Rijksuniversiteit te Groningen, Groningen, Netherlands

[21] Appl. No.: 680,280

[22] Filed: Jul. 11, 1996

Related U.S. Application Data

[63] Continuation of Ser. No. 326,196, Oct. 20, 1994, abandoned.

[30] Foreign Application Priority Data

Oct. 22, 1993 [EP] European Pat. Off. ............. 93202972

[51] Int. Cl.$^6$ .................................................. G01N 27/404
[52] U.S. Cl. ........................... 128/632; 128/630; 128/637
[58] Field of Search .................................... 128/630, 632, 128/633, 635, 637

[56] References Cited

U.S. PATENT DOCUMENTS

| | | |
|---|---|---|
| 3,799,873 | 3/1974 | Brown . |
| 4,192,748 | 3/1980 | Hyden . |
| 4,247,647 | 1/1981 | Barabino et al. . |
| 4,832,034 | 5/1989 | Pizziconi . |
| 5,001,054 | 3/1991 | Wagner .................................... 128/637 |
| 5,399,256 | 3/1995 | Bohs et al. ............................. 204/409 |
| 5,425,868 | 6/1995 | Pedersen ................................ 128/637 |

FOREIGN PATENT DOCUMENTS

| | | |
|---|---|---|
| 0134758 | 3/1985 | European Pat. Off. . |
| WO89/02720 | 4/1989 | WIPO . |

*Primary Examiner*—Angela D. Sykes
*Assistant Examiner*—Stephen Huang
*Attorney, Agent, or Firm*—Hill, Steadman & Simpson

[57] ABSTRACT

In a process and devices or continuously measuring the concentration of an analyte in tissue. The tissue is provided with a hollow fiber having a pore size between the size of the analyte and the size of macromolecules, hollow fiber is perfused with a solution compatible with the tissue, and that solution is supplied from the hollow fiber through a reactor for the analyte. The reactor has a second hollow fiber having a pore size between the size of the analyte and the size of macromolecules, and the second hollow fiber is located in a container which contains macromolecular reactants for detecting the analyte and a signal producing system coupled therewith. The perfusion fluid is fed from the reactor to an eliminator for the analyte, whereby at least 95% of the remaining analyte is removed from the perfusion fluid and the perfusion fluid is reintroduced into said first hollow fiber.

The process and devices operate as a closed circuit and therefore this method can be continued over a longer period of time than known methods, without the need to replace reservoirs.

21 Claims, 5 Drawing Sheets

Calibration Factor: 0.85 Namp/mg/dl
Temp. corr. Factor: 0.03%
Subcut. Glucose conc.: 45% of blood Glucose conc.

Calibration Factor: 0.75 Namp/mg/dl
Temp. corr. Factor: 0.03%
Subcut. Glucose conc.: 45% of blood Glucose conc.

Calibration Factor: 0.75 Namp/mg/dl
Temp. corr. Factor: 0.03%
Subcut. Glucose conc.: 45% of blood Glucose conc.

Calibration Factor: 0.75 Namp/mg/dl
Temp. corr. Factor: 0.03%
Subcut. Glucose conc.: 45% of blood Glucose conc.

Calibration Factor: 0.75 Namp/mg/dl
Temp. corr. Factor: 0.03%
Subcut. Glucose conc.: 45% of blood Glucose conc.

Calibration Factor: 0.75 Namp/mg/dl
Temp. corr. Factor: 0.03%
Subcut. Glucose conc.: 45% of blood Glucose conc.

PROCESSES AND DEVICES FOR CONTINUOUSLY MONITORING LEVELS OF ANALYTE

This is a continuation of application Ser. No. 08/326,196, filed Oct. 20, 1994 now abandoned.

BACKGROUND OF THE INVENTION

1. Field of the Invention

The invention relates to processes for continuously measuring the concentration of an analyte in tissue, as well as to devices for said measurements and to devices which make such measurements and respond by administering an active substance to a patient whose tissue was analyzed.

2. Description of the Prior Art

In medical science, both human and veterinary, a very important criterion for diagnosis and or treatment is the level of certain substances in blood and/or tissue.

The substances of interest (hereinafter referred to as analytes) can be of a wide variety. They can be intermediates or endproducts in metabolism, hormones or hormoneprecursors, antibodies or antigens, pathogens, drugs, etc.

In a number of cases it will be important to keep a continuous check on levels of an analyte in blood and/or tissue.

The analyte which heretofore has been the foremost subject in continuous measurements is glucose in patients suffering from diabetes mellitus.

Though the invention is explained more in detail using glucose as a model system, it is by no means restricted in its use exclusively to that kind of measurement.

Processes and devices for continuously measuring glucose concentrations in (subcutaneous) tissue are known.

It has also been proposed to couple such a measuring device to an insulin pump which can be worn by or implanted in a patient and which then reacts to changes in the blood and/or tissue glucose level.

Generally speaking, these methods and devices are used for patients for whom the classical methods of injecting insulin once or twice a day cannot provide a satisfactory regulation of the glucose (blood) level in the patient.

However, if a "patient friendly" device for measuring analytes such as glucose and dosing a substance such as insulin in reaction to changes in the analyte concentration could be designed, the use of such devices could be far more widespread then this particular group of patients.

Several research groups are involved in designing glucose sensors. One of those research groups is the group of Shichiri of the "First Department of medicine, at the university of Osaka, Japan. This group succeeded [see Diabetologia 24 (1983) 179–184; Biomed. Blochim. Acta 43 (1984), 561–568; Diabetes Care 9 (1986) 298–301] in developing a glucose sensor capable of measuring the glucose concentration in subcutaneous tissue for three days. The small needle-type glucose sensor consists of a platinum electrode covered with immobilized enzyme glucose oxidase. In the reaction of glucose with oxygen in the presence of the enzyme $H_2O_2$ is released which can be measured by this electrode and correlates with the amount of glucose present.

In vitro the electrode gives a current of 1.2±0.4 nA in a 5.5 mmol/l glucose solution. The current is linear with the glucose concentrations, and the time required to obtain 90% of the plateau value is 16.2±6.2 sec.

In first instance, subcutaneous measurements were carried out in dogs, the response showing a delay of 5–15 minutes compared to the direct measurement in blood. The sensitivity of the electrode gradually decreases to 57.4±7% of the initial value after 96 hours measurement. This loss of signal, mainly due to the rapid breakdown of the enzyme, means that the subcutaneously inserted sensor must be replaced at least every three days.

Eventually, Shichiri developed a completely wearable artificial endocrine pancreas (12×15×6 cm, 400 g) consisting of the sensor, a microcomputer which calculates the required infusion rate of insulin, and a dual-syringe driving system. This apparatus is capable of controlling the blood glucose concentration in depancreatized dogs for three days. Shichiri then proceeded to measurement in subcutaneous tissue of diabetics. The subcutaneously measured glucose values are, on average, 10% lower than those of blood, but there is a good correlation between the two values in the range of from 60 to 400 mg/dl glucose. Then, patients suffering from diabetes were provided with the complete artificial pancreas, using a self-developed subcutaneous insulin infusion algorithm. Only one representative patient in which the glucose was controlled by the sensor for two days is mentioned.

Another research group is directed by M. Kessler of the Institute for Physiology and Cardiology of the University of Erlangen-Nuremberg. The glucose sensor they developed [Hepatogastroenterol. 31 (1984) 285–288] also operates through an enzymatic conversion of glucose by means of glucose oxidase, followed by measuring the resulting $H_2O_2$ using an electrode with a gold anode covered with three membranes. A dialysis membrane permeable to glucose, gases and inorganic ions but impermeable to larger molecules, such as proteins, serves as a selector. In the next layer there is an enzyme membrane functioning as a kind of reaction space. Contained therein is the immobilized enzyme glucose oxidase. A sealing lipophilic membrane with incorporated proton carrier molecules is closest to the gold anode. In the presence of the enzyme the glucose diffusing through the dialysis membrane reacts with oxygen, thus forming $H_2O_2$. The $H_2O_2$ is oxidized at the gold anode so as to form two protons. These are eliminated by the proton carriers. With this sensor Kessler carried out measurements in the peritoneum of anesthetized rats. He found a good correlation between the glucose values measured in the peritoneum and the real blood glucose values. Dimensions of the electrode are not mentioned, but an electrode suitable for implantation in human beings is not yet available.

A. Müller and P. Abel of the Zentralinstitut für Diabetes "Gerhardt Katsch" from Karlsberg (GDR) (Prof. U. Fischer) also have a glucose oxidase/$H_2O_2$ sensor available [Biomed. Blochim. Acta 43 (1984) 577–584; Biomed. Biochim. Acta 45 (1986) 769–777]. Again the immobilized enzyme is attached to the electrode (Pt) surface. The electrode is covered by respectively a hydrophobic and a hydrophilic membrane as a selector for the glucose. After an initial unstable period of 24 hours this electrode gives a stable signal, i.e., a current of 0.02–6.8 nA, depending on the glucose concentration. It is 7 cm in length and has a diameter of 2–4 mm. The electrode was implanted in 6 dogs and the glucose was measured. The ratio between glucose concentrations in blood and in tissue then varies from 33 to 70%. Besides this large variation, failures occur frequently so that a good calibration is not possible.

All the glucose sensors hitherto discussed that have already reached the experimental in vivo stage are based on a system with immobilized enzyme glucose oxidase on an electrode. This has the advantage that the electrode can be miniaturized and readily implanted in whole. However, an important drawback is that under those conditions the enzyme stability is limited and consequently frequent replacement (3–4 days) of the electrode is necessary. Another requirement in the technique of immobilization is that each electrode must be calibrated individually and that it takes several hours to a day before the electrode can give a stable signal.

In European Patent Application No. 88908397.8 a device is disclosed which, like the devices of the invention does not use an implanted electrode, but uses an implant of a hollow fiber, which is suitable for microdialysis.

This device however, requires a reservoir of perfusion fluid and a reservoir for fluids hollow fiber. In other words it is not a closed circuit and both reservoirs need to be changed frequently.

SUMMARY OF THE INVENTION

The present invention provides a process and devices for continuously measuring the concentration of an analyte in tissue, wherein the tissue is provided with a hollow fiber having a pore size between the size of the analyte and the size of macromolecules, the hollow fiber is perfused with a solution compatible with the tissue, and that solution is led from the hollow fiber through a reactor for the analyte. The reactor has a second hollow fiber having a pore size between the size of the analyte and the size of macromolscules, the second hollow fiber being located in a container which contains macromolecular reactants for detecting the analyte and which has a signal producing system coupled therewith. The perfusion fluid is led from the reactor to an eliminator for the analyte, whereby at least 95% of the remaining analyte is removed from the perfusion fluid and the perfusion fluid reintroduced into the first hollow fiber.

This makes the sensing system a dynamic closed loop circuit and therefore this method can be continued over a longer period of time than the methods of the prior art, without the need to replace reservoirs.

To create a closed loop microdialysis based (glucose) sensor it is absolutely necessary to remove or eliminate substantially all of the analyte (glucose) (>95%) in the dialysate before re-entering the body microdialysis circulation, to avoid accumulation of analyte (glucose) within the measuring circuit. Therefore an analyte (glucose) eliminating device, hereafter called glucose-eliminator (GE) has to be integrated within the dialysis circuit, either before or after the measurement cell.

Also very important is that the macromolecule (usually not of human origin) is not present in the perfusion fluid in any significant amounts. It has been shown that although the pore size of hollow fibers used in these methods reportedly is too small for such macromolecules, there will always be leakage of macromolecules. Therefore the device and/or method as disclosed in European Patent Application No. 88908397.8 would not be suitable for designing a closed circuit since the macromolecule would leak into the tissue and give rise to allergic reactions, inflammation and/or hypersensitivity for the macromolecules.

In the methods of the present invention the macromolecules are separated from the perfusion fluid by the second hollow fiber which is permeable for the analyte, but not for the macromolecules.

The perfusion fluid is separated from the tissue by the first hollow fiber. If any or both of the hollow fibers leak some macromolecules, the amount of macromolecules coming into contact with the tissue would still probably be too small to lead to serious problems.

In order to exclude even that small risk of body reaction to the macromolecules, it is preferred that a filter for such macromolecules is present in the fluid circuit, a suitable filter in a number of cases (for glucose oxidase for instance) is an active carbon filter.

In many instances the macromolecule used to react with and thereby detect the analyte can be an enzyme for which the analyte is a substrate. This is preferred because an enzyme can perform a multitude of conversions and therefore the capacity to detect analyte will be sufficient for a prolonged period of time. When antibodies or other reagents are used, they usually will only bind a couple of analyte molecules per macromolecule and thus have a much more limited capacity. When analytes are to be detected which are only present in trace amounts, this may suffice for a long enough interval. In the case of glucose measurements an enzyme is preferred.

A suitable enzyme which uses glucose as a substrate is glucose oxidase.

Glucose and oxygen react under the influence of glucose oxidase (GOD) according to the following scheme. One can either measure the amount of oxygen remaining or the amount of $H_2O_2$ produced.

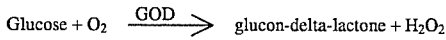
$$\text{Glucose} + O_2 \xrightarrow{\text{GOD}} \text{glucon-delta-lactone} + H_2O_2$$

For measuring continuously in vivo this method has a few drawbacks:

1) The 02 concentration in the fluid to be measured (saturated in water or body fluid) is not sufficient. At glucose concentrations of 100 mg/dl or more the $O_2$ concentration is already zero and glucose is no longer measurable. Therefore, the concentration of glucose participating in the enzymatic reaction should be restricted with respect to the $O_2$ concentration.

2) The enzyme GOD deteriorates during the measurement, especially by the presence of hydrogen peroxide, that is produced in the reaction.

3) $H_2O_2$ diffuses easily into the body causing inflammation reactions. Even the enzyme GOD diffuses into the body by a few large pores that are inevitably present in the ultrafiltration membranes currently available.

The use of a microdialysis system can prevent or circumvent the above mentioned problems:

1) A dilution of the glucose concentration in the body is easily achieved by selecting short hollow fibers in the probe or by adapting the perfusion rate.

2) An excess of enzyme, that may replace degraded enzyme, is easily introduced in the microdialysis system. For instance, a far higher concentration of dissolved enzyme may be applied, but also methods dosing the enzyme in a controlled way can be useful to extend the sensor lifetime significantly.

3) Diffusion of $H_2O_2$ and/or enzyme into the body can be prevented by using the microdialysis system as an interface between the body and the measurement, in which the "hollow fiber" probe in the body is perfused only by a body compatible fluid.

It is preferred according to the invention to measure the used amount of oxygen, preferably using an electrode. This has the advantage that less stringent requirements need to be imposed on the quality of the enzyme employed. If the glucose sensor would be based on a measurement of the resultant amount of hydrogen peroxide, traces of the enzyme catalase which catalyzes the breakdown of hydrogen peroxide could adversely affect the accuracy of the measurement. A second problem associated with a measurement of the resultant amount of hydrogen peroxide is that the dialysis fluid containing the $H_2O_2$ formed is to be immediately contacted with the electrode, and thus other substances in the dialysis fluid may have a disturbing effect on the measurement. This last-mentioned drawback could possibly be removed by using special membranes, e.g., specific cellulose ester membranes, but a perfect separation of dialysis fluid and electrode which only allows hydrogen peroxide to pass is hard to obtain. If, however, the used amount of oxygen is measured, the dialysis fluid can be perfectly kept separated from the electrode by means of a membrane which is only permeable to gases, such as a Teflon® membrane, and the measurement can be carried out in a well defined electrolyte, such as a potassium phosphate buffer of $1/15M$ $K_2HPO_4$.

In this context it is preferred according to the invention that a measuring cell be used which has an operating electrode, an electrolyte space filled with electrolyte and a reference electrode, and the perfusion fluid is passed along the measuring cell via a flow chamber provided in a flow element. The flow chamber has an inlet for the; perfusion fluid coming from the first hollow fiber and an outlet for the perfusion fluid to return to the first hollow fiber and is separated from the measuring cell by a membrane permeable to oxygen gas. For the measuring cell, it is preferred that an operating electrode of a noble metal, such as gold, silver and preferably platinum, and a reference electrode of silver are used, that the electrolyte employed is a potassium phosphate buffer, preferably $1/15M$ $K_2HPO_4$, that the membrane permeable to oxygen gas is a hydrophobic membrane, preferably a Teflon® membrane, and that a voltage negative with respect to the reference electrode of about 0.6 V is applied to the; operating electrode.

Preferably the enzyme reactor, containing excess glucose oxidase and catalase, should convert all glucose present in the dialysate before passing the oxygen electrode (and function as the eliminator). In that case the measuring principle, automatically prevents glucose accumulation. For reasons of increasing lag times and delay, however, the enzyme reactor is limited in size and probably will not be sufficient to eliminate all glucose.

The reactor comprises a non-gas permeable tube (for instance polyethylene: i.d. 0.35 mm) through which a semi-permeable membrane, preferably regenerated cellulose (o.d. 200 μm; MWCO=9000 Dalton), is guided. Around the membrane the enzyme solution is located. Glucose diffuses from the interluminal space into the enzyme layer and is converted by the enzyme glucose oxidase. The resulting decrease in oxygen concentration is reflected in the dialysate and is measured afterwards with the oxygen electrode. To guarantee a rapid measurement the diameter of the enzyme reactor should be as small as possible to promote rapid reflection of the decreased oxygen concentration into the interluminal space of the dialysis fiber.

A comparable design can be used as glucose eliminator to be integrated in the microdialysis circuit, preferably between the measuring cell (oxygen electrode) and the pump.

Glucose oxidase or any other enzyme converting glucose (for example, glucose dehydrogenase) can be integrated in such an eliminator. Outer and inner diameters as well as type of the membranes used in such an eliminator are less important than in the enzyme reactor that is providing the measurement.

More cellulose membranes can be glued into an enzyme compartment to allow glucose to react within the eliminator. The enzyme solution should preferably contain catalase to eliminate the hydrogen peroxide, formed in the glucose oxidase reaction.

The enzyme based glucose eliminator can contain glucose oxidase and catalase in solution, but also other ways of enzyme immobilization can be applied, such as fitting the enzyme in a gel or immobilize it on the inner wall of a tube. Contact time of the perfusion fluid with the enzyme (reactor) should be long enough to guarantee that all glucose is eliminated. Therefore dimensions of the glucose eliminator can vary widely in length and diameter.

A suitable glucose eliminator comprises a Teflon® tube (i.d. 0.96 mm, length 80 mm), through which four cellulose fibers are guided. Excess glucose oxidase and catalase (>40.000 U/ml) are dissolved in saline (0.9% NaCl in water), surrounding the cellulose membranes. Since the eliminator is not meant to provide a measurement preferably oxygen permeable tubes are used for the construction, since sufficient oxygen is needed for the enzymatic reaction.

Other enzymes, like glucose dehydrogenase, can be used in the eliminator, provided that all co-factors and other reagents that are required are also present.

Other ways of eliminating glucose can be used to get rid of the glucose within the dialysate. Destruction by the application of heat, for example from a glowing filament is a possible procedure, although energy consuming. Another way of consuming the dialysate glucose is the use of micro-organisms. Several types of micro-organisms are known to be selective consumers of sugars, so integration into a glucose eliminator could be possible. When aiming at in vivo use, additional safety measures should be made if micro-organisms are involved.

Another strategy to eliminate glucose within the microdialysis circuit is the use of specific chemical reagents to adsorb glucose or to react directly with glucose. A disadvantage of those type of elimination procedures is the fact that there will be a limit to their function. Adsorption capacity is limited and thus dependent on the amount of glucose which is present. The same is true for non-enzymatic chemical reactions. When an excess amount of a selective glucose eliminating chemical substance can be integrated within a device, however, such a design might be suitable.

The hollow fibers used for microdialysis must be permeable for the analyte (glucose).

Preferably a fiber of saponified cellulose ester having a molecular weight cut off value of about 10 kD is used. However, other types of materials are also useful, such as hollow fibers of polysulfone and acrylic copolymer (Amicon). The preferred cellulose fiber, however, is stronger and more flexible and can be inserted into the body more easily than the thicker and more vulnerable Amicon fiber.

With regard to sizes, it is preferred that a hollow fiber is used having an inner diameter of 100–500 μm, preferably 120–200 μm, an outer diameter of 130–550 μm, preferably 150–250 μm, and being 0.1–3 cm, preferably 0.5–2.5 cm, in length.

The nature of the tubes, leading to and from the first hollow fiber and otherwise present as connections between different elements of the devices, is not critical, provided they are airtight. Polyethylene tubes are preferred. As for their sizes, it is preferred that the airtight supply and discharge tubes have an inner diameter of 0.2–0.6 mm, preferably 0.25–0.35 mm, and an outer diameter of 0.4–1.0 mm, preferably 06.–0.8 mm.

The length of the airtight discharge tube between the hollow fiber and the reactor must preferably be as small as possible so as to enable a rapid response. It is preferred that the airtight discharge tube between the hollow fiber and the reactor is 1–10 cm, preferably 1–5 cm, in length.

With regard to the measuring element, for achieving a high accuracy of the glucose sensor it is preferred that a flow chamber be used with the sizes, shapes and positions of the perfusion fluid inlet and outlet being such that substantially no dead spaces occur. The exposed surface of the operating electrode which is separated from the perfusion fluid by the membrane permeable to oxygen (or to $H_2O_2$) may be transverse to the direction of flow of the perfusion fluid or may be in line with the perfusion fluid inlet opening; the distance between the inlet opening and the exposed surface of the operating electrode preferably is less than 5 mm, and most preferably less than 1 mm.

The invention further provides an artificial pancreas, which includes, in addition to the devices already described, a regulable injection system for introducing active substances, such as insulin, into the organism, a calculating and regulating system for calculating the glucose concentration in the subcutaneous tissue on the basis of the measuring values of the measuring cell and an associated calibration curve, by means of an algorithm, the characteristic and relevant parameters of which are contained in a mathematical model, and thereby determining the amount of active substance to be supplied, and for controlling the regulable injection system in such a manner that the glucose (analyte) concentration in the tissue and/or in the blood remains within predetermined values. Preferably, the calculating unit also has an alarm function for providing a warning in case of extreme glucose concentrations in the body and in case of failures. The calculating unit can also have the secondary task of monitoring the curve of the memory concentration and insulin supply, storing same in the local memory and transferring same upon command of an external system to other data processing systems.

DESCRIPTION OF THE PREFERRED EMBODIMENTS

Figure 1:
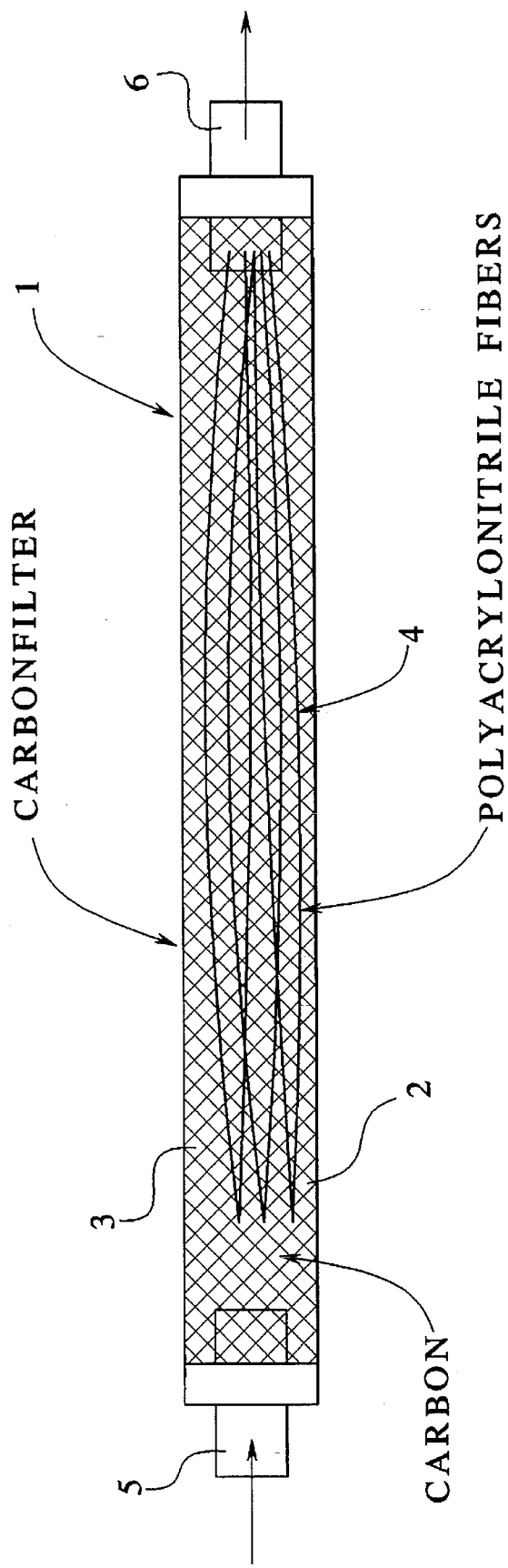
FIG. 1 shows a carbon filter suitable for use in the method and devices in accordance with the principles of the present invention.

FIG. 1 shows a carbon filter 1 which can be used in the methods and the devices according to the invention. The active carbon 2 is present in a polyethylene tube 3 provided with polyacrilonitrile fibers 4. At each end the filter is connected with another element of the device through respective airtight polyethylene tubes 5 and 6.

Figure 2:
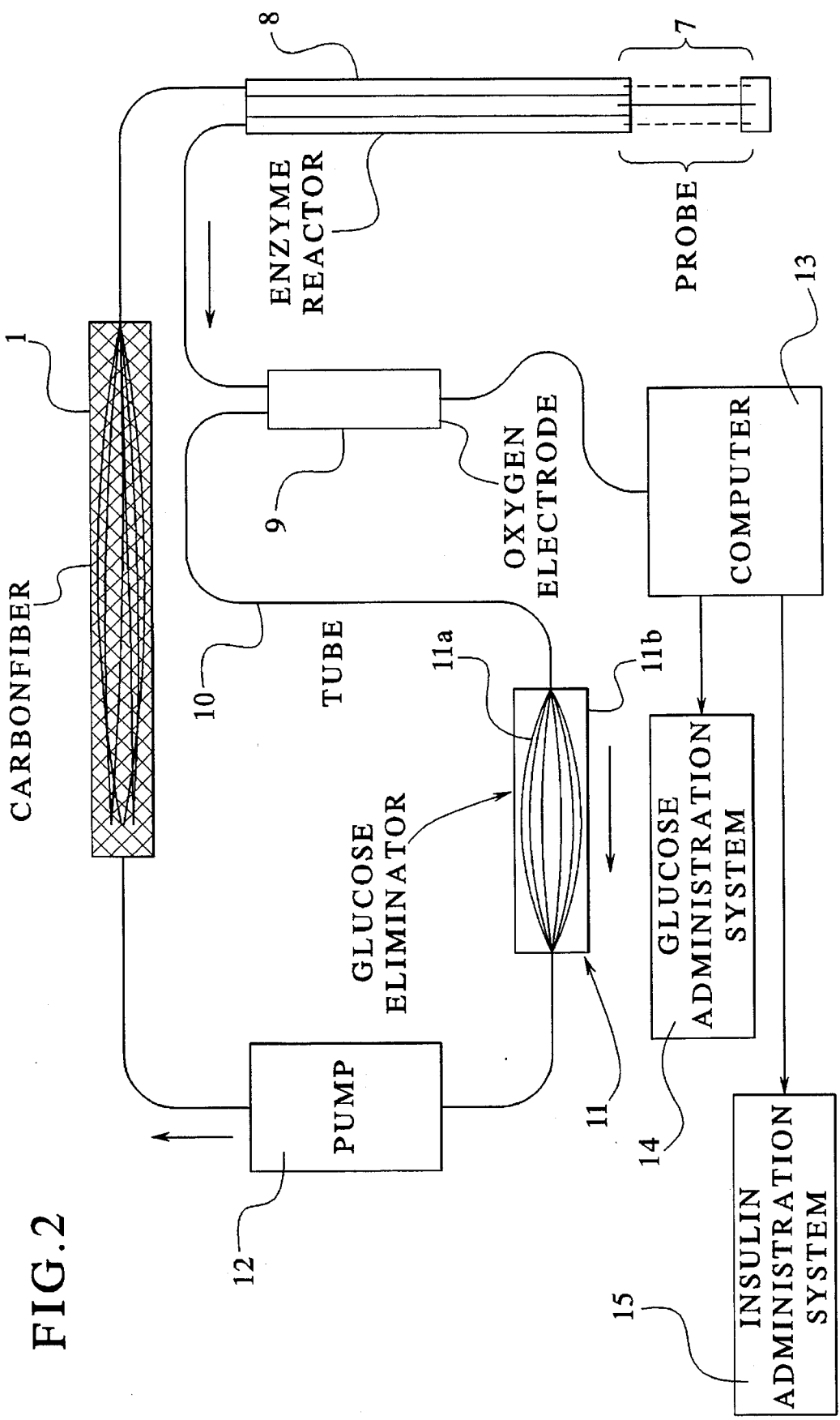
FIG. 2 a schematic block diagram of a device for measuring glucose levels constructed in accordance with the principles of the present invention.
Figure 3A:
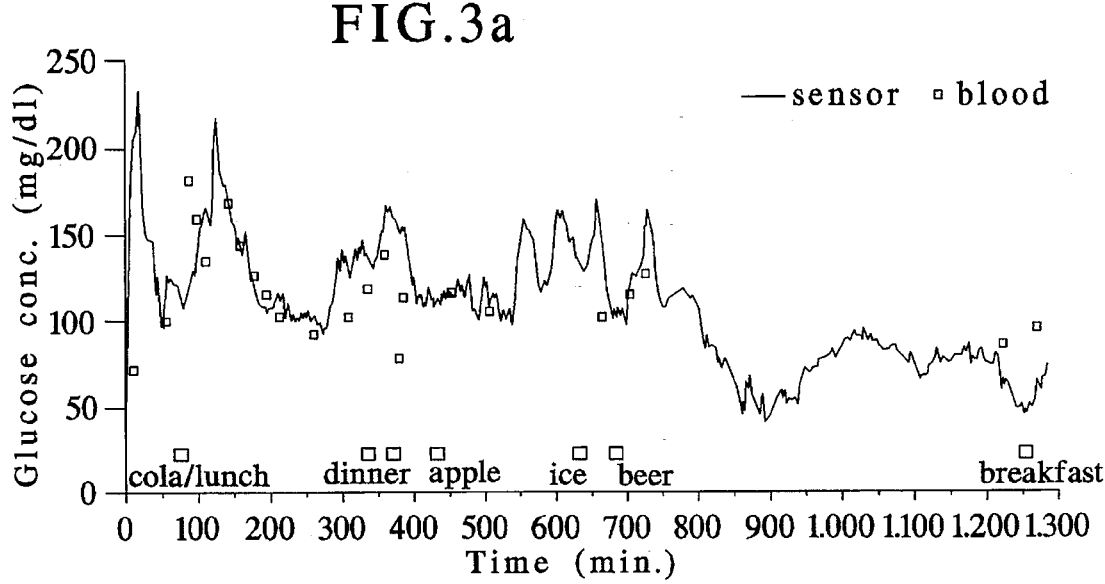
FIG. 3a shows the daily output, for the first day, of a wearable device constructed in accordance with FIG. 2, worn by a healthy person during testing of the device.
Figure 3B:
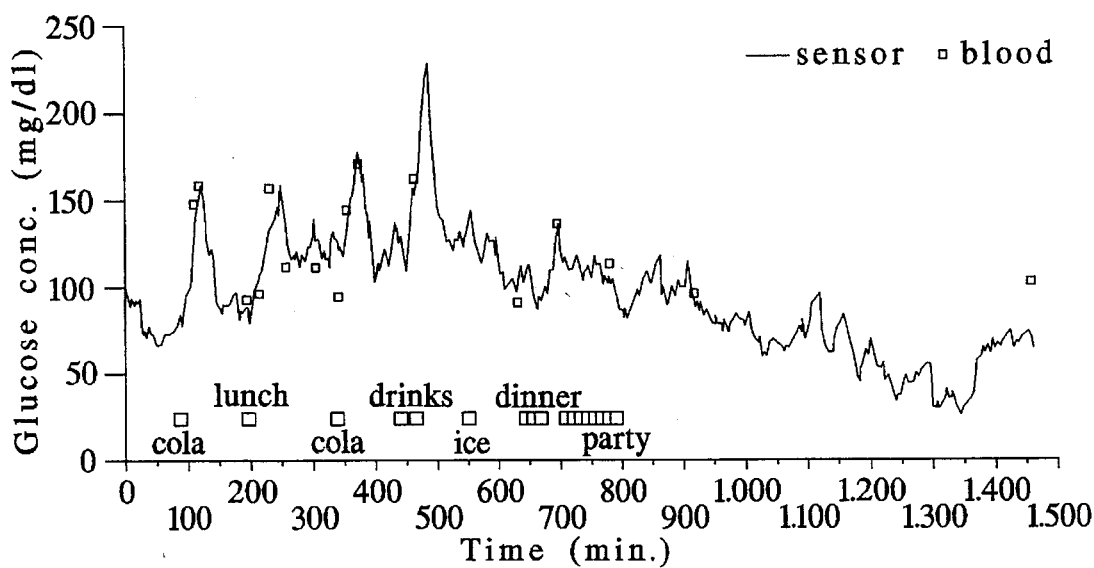
FIG. 3b shows the daily output, for the second day, of a wearable device constructed in accordance with FIG. 2, worn by a healthy person during testing of the device.
Figure 3C:
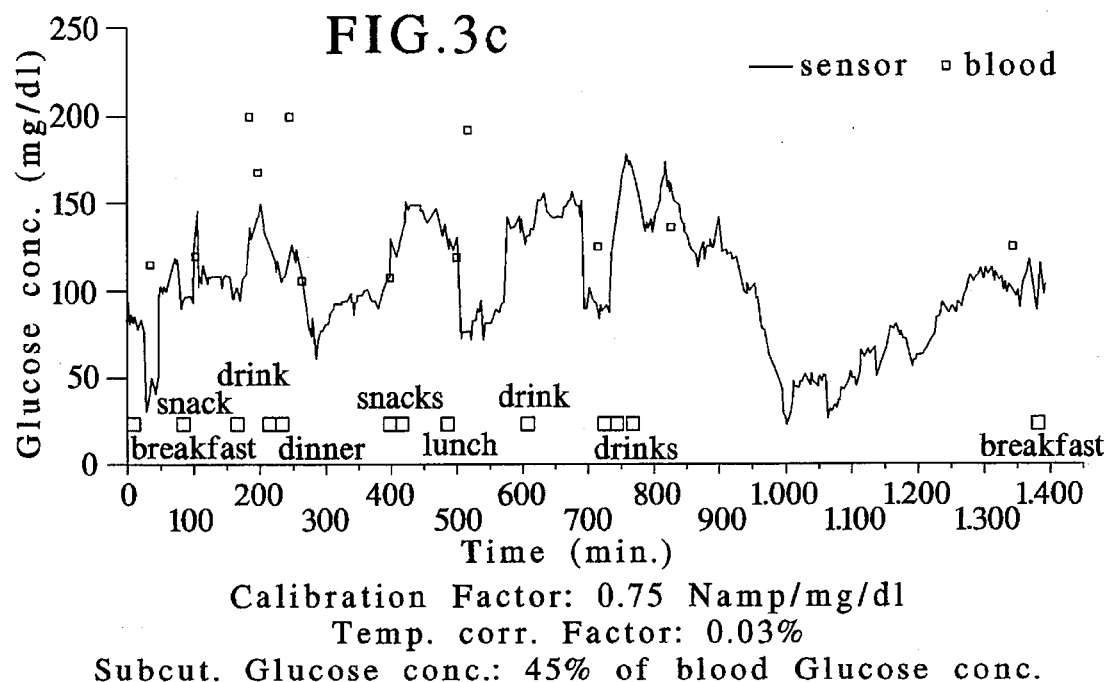
FIG. 3c shows the daily output, for the third day, of a wearable device constructed in accordance with FIG. 2, worn by a healthy person during testing of the device.
Figure 3D:
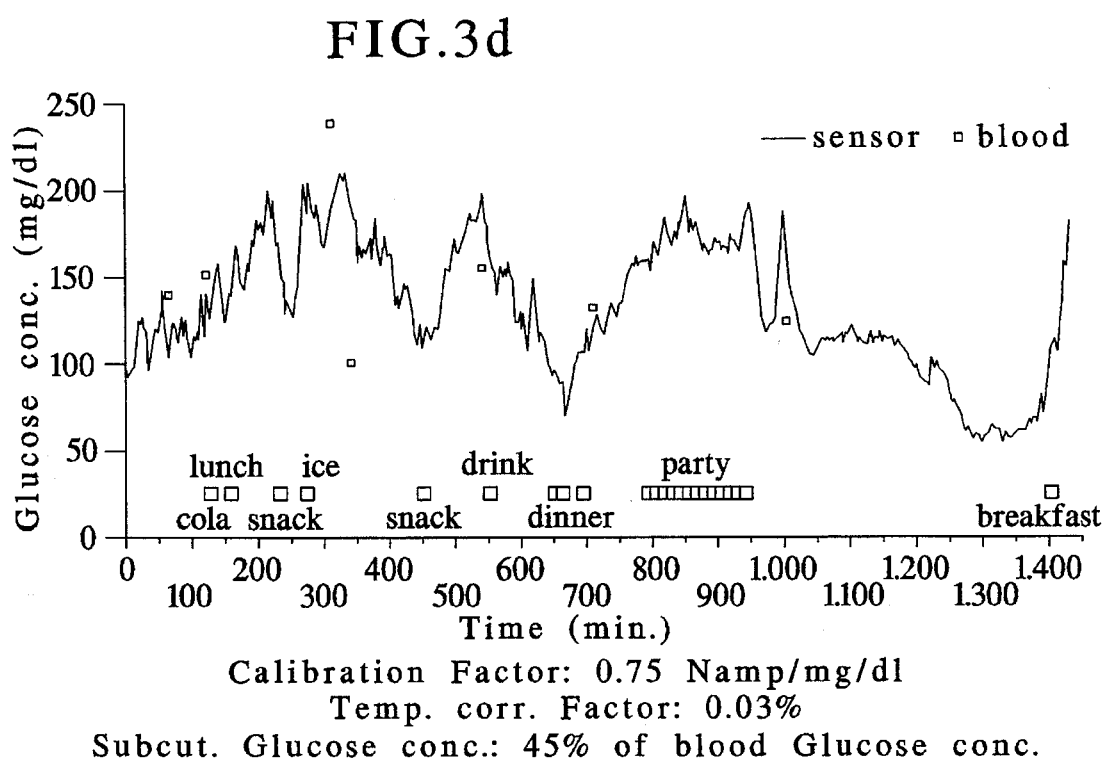
FIG. 3d shows the daily output, for the fourth day, of a wearable device constructed in accordance with FIG. 2, worn by a healthy person during testing of the device.
Figure 3E:
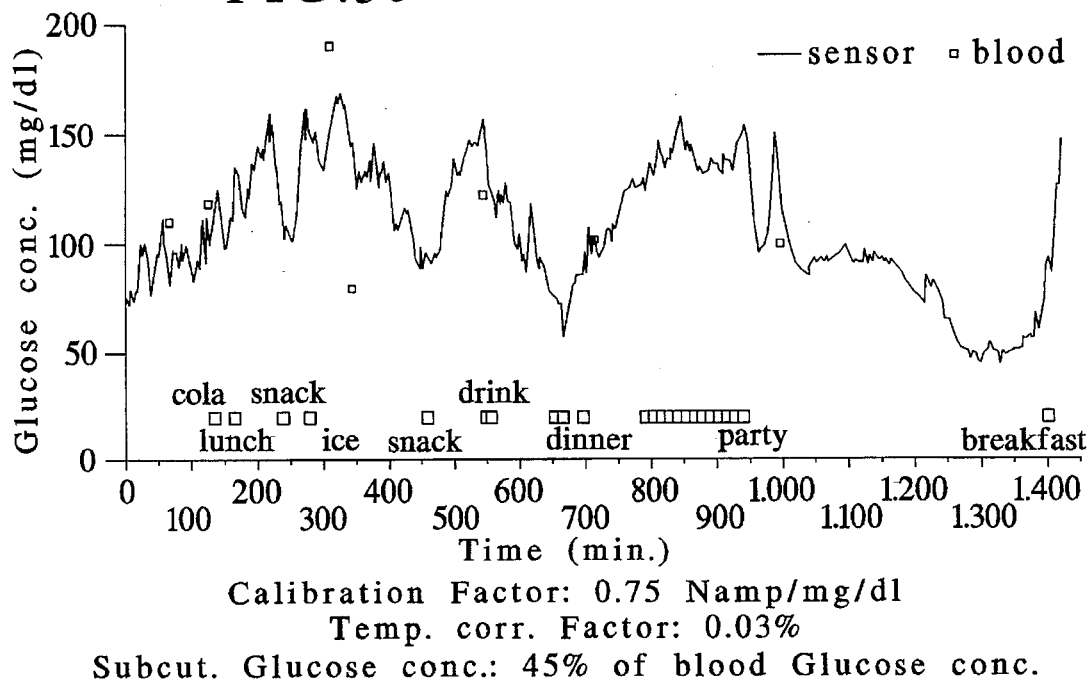
FIG. 3e shows the daily output, for the fifth day, of a wearable device constructed in accordance with FIG. 2, worn by a healthy person during testing of the device.
Figure 3F:
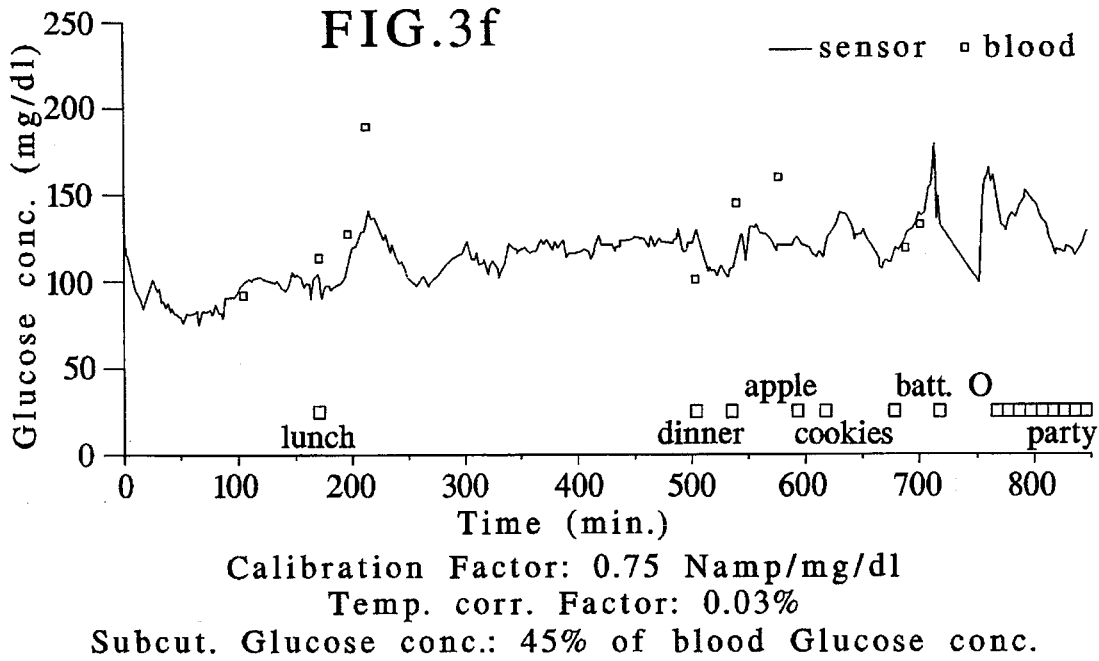
FIG. 3f shows the daily output, for the sixth day, of a wearable device constructed in accordance with FIG. 2, worn by a healthy person during testing of the device.

FIG. 2 shows a device according to the invention for measuring glucose levels, wherein the probe 7 represents the hollow fiber to be implanted subcutaneously for microdialysis. The probe 7 is connected to the rest of the device in a way that it can be easily disconnected and reconnected so that when the enzyme or the filter or the eliminator need to be replaced, no re-implantation is necessary. In FIG. 2 the arrows indicate the flow direction of the perfusion fluid. Downstream from the probe 7, connected therewith through an airtight tube, is the enzyme reactor 8, wherein the enzyme is separated from the perfusion fluid by a membrane permeable for glucose but not for glucoseoxidase. Downstream from the enzyme reactor 8, the oxygen produced in the reactor 8 is measured by an oxygen electrode 9, as indicative of the detected level of glucose which is electrically connected to a signal producing system including a computer 13 outside the loop. The computer 13 may be connected to an insulin administration system 14 and/or to a glucose administration system 15 which respectively administer insulin and/or glucose to a patient whose tissue was analyzed in accordance with the invention. The insulin and/or glucose are administered at time and volumes dependent on the level of the signal from the electrode 9, corresponding to the detected glucose level. From the electrode 9 the perfusion fluid is supplied through a Teflon® tube 10 to the glucose eliminator 11, which contains a number of fibers 11a through which the fluid is lead, which are permeable for glucose, but not for glucose oxidase. Surrounding those fibers 11a is a chamber 11b in which glucose oxidase is located. Downstream from the eliminator 11, a pump 12 is provided, and downstream from the pump 12 the carbon filter 1 according to FIG. 1 is located. The perfusion fluid is fed from the filter 1 to the probe 7.

FIGS. 3a through 3f respectively show the daily output of a wearable device according to FIG. 2, when implanted in a healthy person. In the graphs in FIGS. 3a through 3f the curve represents the glucose levels as measured by the device, the open squares are glucose levels measured in blood using standard methods. At the bottom of the graph the filled squares give the relevant events for the glucose levels. The measurements were continued with one device through six days.

EXAMPLES

In Vitro Experments

When the glucose sensor is used in vivo, it is of great importance that no Glucoseoxidase (GOD) enzyme molecules can diffuse into the body, because GOD can trigger an immunoallergic reaction and give local irritation because of $H_2O_2$ production. Even though the enzyme solution is kept outside the perfusion fluid by means of a regenerated cellulose membrane, it is possible for some GOD molecules to enter the perfusion fluid. This is possible because each membrane has some so-called "pin-holes", i.e., very large pores, through which GOD molecules can leak into the perfusion fluid. By the integration of a "carbon filter" in the flow system it is possible to remove the GOD molecules from the perfusion fluid. Preferably this carbon filter is placed between the pump and the dialysis probe as shown in FIG. 2. In this way the carbon filter also damps the pump pulse, thus creating a more constant perfusion flow.

The carbon filter (FIG. 1) consists of a polyethylene tube (i.d. 3 mm, length 5 cm) into which a bundle of three polyacrylonitrile fibers is placed. It is provided with approximately 50 mg of active carbon. Because of this extra filtration step, the perfusion fluid stays longer in the carbon filter. This enables the carbon to adsorb the GOD molecules more effectively. The capacity of the carbon filter can be increased by increasing the amount of carbon.

To determine how much GOD Could be removed by the active carbon the following experiments were performed. To demonstrate the presence of GOD, Perid®- sticks impregnated with glucose were used. These sticks turn blue/green when GOD molecules are present in the test fluid. It is possible to detect a GOD enzyme concentration of 0.025 units GOD/ml.

A first experiment was conducted to show that carbon indeed adsorbs GOD molecules. In this experiment carbon filters were used as described above except for the bundle of polyacrylonitrile fibers. These carbon filters were perfused with a GOD solution of 30 units GOD/ml at a flowrate of 0.6 ml/hour. The perfusate was tested every hour for the presence of GOD molecules. After two and a half days, GOD molecules were found in the perfusate. It was concluded that active carbon indeed adsorbs the GOD enzymes but the amount of adsorption depends on the concentration of active carbon and of the GOD concentration in the perfused GOD solution and the time that these GOD molecules are present in the carbon filter.

In a second experiment it was determined how many GOD units are adsorbed by a milligram of active carbon. Carbon filters with a known amount of active carbon were perfused with a solution with a known concentration of GOD. No polyacrylonitrile fibers were used in these filters. Every hour a sample was taken and checked for the presence of GOD molecules. The concentration of GOD adsorbed by one milligrain of carbon was calculated. It appears that on average 1.8–0.2 units of GOD are adsorbed by 1 milligrain of active carbon.

When the glucose sensor is used in vivo or in vitro, the perfusion fluid is regularly checked for GOD molecules. A perfusion sample is taken for and after passing the carbon filter. In practice the carbon filters work very well for a period of at least a month; even when there are GOD molecules present in the sample before passing the carbon filter, no GOD molecules were detected in the sample downstream of the filter. The durability of the carbon filters can be increased by using a larger amount of carbon and the application of a bundle of polyacrylonitrile fibers. We have shown that in this way the purification of the perfusion fluid can be acquired and that the danger of GOD-leakage into the body can be prevented.

In Vivo Experiments

These experiments were performed with the closed loop microdialysis system shown in FIG. 2. Ambulant in vivo experiments were performed on nine healthy volunteers. The mean duration of these in vivo trials was about 3 days. The longest in vivo experiment lasted for 6 days. These experiments were performed in such a way that the volunteers could conduct their daily life wearing the sensor system, The glucose sensors (FIG. 2) used in these in vivo experiments were in vitro calibrated. The glucose concentration in the subcutaneous tissue is about 45%±9 of the blood value. With the data found in the in vitro calibration, the glucose concentration in the blood can be calculated at any moment.

The glucose probe of the glucose sensor was placed subcutaneously in the abdominal fatty tissue by means of a 16 gauge catheter and fixed in place with a plaster. Containers for the flow system and the portable data processor were worn in a belt around the subject's waist. The subjects were asked to measure their blood sugar level regularly by means of a commercially available wearable blood sugar meter. These values give an indication of the subject's blood sugar levels and were compared with the sensor measurements. The subject also noted what he or she ate and what he or she did for the duration of the test, as far as relevant. These data were plotted in a graph to check the sensors, functioning. None of the subjects exhibited an inflammation reaction at the sensor insertion side.

Although modifications and changes may be suggested by those skilled in the art, it is the intention of the inventors to embody within the patent warranted hereon all changes and modifications as reasonably and properly come within the scope of their contribution to the art.

We claim as our invention:

1. A process for continuously measuring a concentration of an analyte in tissue, comprising the steps of:

disposing a hollow fiber in contact with said tissue having a pore size between a size of said analyte and a size of macromolecules;

perfusing said hollow fiber with a macromolecule-free prefusion fluid compatible with said tissue so that said analyte enters said perfusion fluid through said hollow fiber;

feeding said perfusion fluid with said analyte therein from said hollow fiber through a reactor for said analyte, said reactor including a further hollow fiber having a pore size between said size of said analyte and said size of macromolecules, said further hollow fiber being disposed in a non-porous container containing macromolecular reactants so that said perfusion fluid with said analyte therein is exposed to said macromolecular reactants exclusively in said container;

detecting said analyte using macromolecular reactants exclusively in said container and generating an electrical signal corresponding to a detected level of said analyte;

feeding said perfusion fluid from said reactor to an eliminator and, in said eliminator, removing at least 95% of said analyte from said perfusion fluid; and reintroducing said perfusion fluid, after removing said analyte therefrom, in a closed loop into said hollow fiber with 5% or less of said analyte therein.

2. A process as claimed in claim 1 comprising the additional step of:

disposing a filter in a stream of said perfusion fluid between said reactor and a location at which said perfusion fluid is reintroduced into said hollow fiber in contact with said tissue.

3. A process as claimed in claim 2 wherein the step of disposing a filter in said perfusion fluid stream is further defined by disposing an active carbon filter in said perfusion fluid stream.

4. A process as claimed in claim 1 wherein the step of removing said analyte from said perfusion fluid in said eliminator comprises reacting said perfusion fluid in said eliminator with an enzyme for which said analyte is a substrate.

5. A process as claimed in claim 1 wherein the step of detecting said analyte in said reactor comprises reacting said perfusion fluid in said reactor with an enzyme for which said analyte is a substrate.

6. A process as claimed in claim 1 wherein said analyte is glucose, wherein the step of disposing a hollow fiber in contact with said tissue comprises disposing a hollow fiber in contact with said tissue having a pore size between a size of glucose and a size of macromolecules, wherein the step of feeding said solution is further defined by feeding said solution from said hollow fiber through a reactor for glucose, said reactor including a further hollow fiber having a pore size between said size for glucose and said size of said macromolecules, wherein the step of detecting said analyte comprises detecting glucose using macromolecular reactants in said container and generating an electrical signal corresponding to a detected level of glucose, and wherein the step of removing at least 95% of said analyte from said perfusion fluid comprises removing at least 95% of glucose from said perfusion fluid.

7. A process as claimed in claim 6 wherein the step of detecting glucose comprises detecting glucose by reacting glucose with a glucose oxidase in said container to generate said electrical signal corresponding to said detected level of glucose.

8. A process as claimed in claim 7 wherein the step of detecting glucose comprises detecting glucose by reacting glucose with a glucose oxidase in said container thereby resulting in a decreasing amount of $O_2$ in said perfusion fluid dependent on the reaction of glucose with said glucose oxidase, and wherein the step of generating said electrical signal comprises generating an electrical signal corresponding to the decreasing amount of $O_2$ in said perfusion fluid.

9. A process as claimed in claim 8 wherein the step of detecting glucose comprises measuring said decreasing amount of $O_2$ with a measuring cell having an operating electrode, an electrolyte space filled with electrolyte and a reference electrode, passing said perfusion fluid through said measuring cell, and separating said $O_2$ from said perfusion fluid through an oxygen permeable membrane.

10. A process as claimed in claim 9 wherein the step of measuring said decreasing amount of $O_2$ with a measuring cell comprises measuring said decreasing amount of $O_2$ with a measuring cell having a noble metal operating electrode and a silver reference electrode.

11. A process as claimed in claim 6 wherein the step of removing at least 95% of said glucose from said perfusion fluid comprises removing at least 90% of glucose from said perfusion fluid by reacting the glucose with a glucose oxidase.

12. A process as claimed in claim 11 wherein the step of removing at least 90% of glucose from said perfusion fluid comprises removing at least 90% of glucose from said perfusion fluid by reacting the glucose with catalase.

13. A device for continuously measuring a concentration of an analyte in tissue, comprising:

a hollow fiber adapted for contact with tissue, said hollow fiber having a pore size between a size of said analyte and a size of macromolecules;

means for perfusing said hollow fiber with a macromolecule-free perfusion fluid compatible with said tissue for causing said analyte to enter said perfusion fluid through said hollow fiber;

a reactor for said analyte, said reactor including a nonporous container containing macromolecular reactants and containing a further hollow fiber having a pore size between said size of said analyte and said size of macromolecules;

means for feeding said perfusion fluid from said hollow fiber through said reactor for exposing said perfusion fluid with said analyte therein to said macromolecular reactants exclusively in said container;

means for detecting said analyte using macromolecular reactants exclusively in said container and for generating an electrical signal corresponding to a detected level of said analyte;

eliminator means for removing at least 95% of said analyte from said perfusion fluid;

means for feeding said perfusion fluid from said reactor to said means for eliminating; and means for reintroducing said perfusion fluid, after the removal of said analyte therefrom in a closed loop, into said hollow fiber adapted for contact with said tissue with 5% or less of said analyte therein.

14. A device as claimed in claim 13 further comprising a filter for said perfusion fluid disposed downstream from said reactor.

15. A device as claimed in claim 14 wherein said filter comprises an active carbon filter.

16. A device as claimed in claim 13 wherein said means for detecting said analyte and for generating an electrical signal comprise a noble metal operating electrode and a silver reference electrode disposed in an electrolyte solution, for measuring a decrease in oxygen in said perfusion fluid, and further comprising a membrane in contact with said perfusion fluid permeable for oxygen.

17. A device as claimed in claim 16 wherein said electrolyte solution comprises a potassium phosphate buffer solution.

18. A device as claimed in claim 13 wherein said macromolecular reactant comprises a glucose oxidase and wherein said analyte comprises glucose.

19. A device as claimed in claim 18 further comprising dosage means for administering glucose to a patient in whom said tissue is disposed dependent on a level of said electrical signal corresponding to said detected level of said analyte.

20. A device as claimed in claim 19 wherein said dosage means comprises means for administering insulin dependent on said level of said electrical signals corresponding to said detected level of said analyte.

21. A device as claimed in claim 17 further comprising means for administering glucose to a patient in whom said tissue is disposed dependent on a level of said electrical signal corresponding to said detected level of said analyte, and means for administering insulin to said patient dependent on said level of said electrical signal corresponding to said detected level of said analyte.

\* \* \* \* \*